United States Patent
Yin et al.

(10) Patent No.: US 11,350,844 B2
(45) Date of Patent: Jun. 7, 2022

(54) SYSTEM AND METHOD FOR GENERATING NONALCOHOLIC FATTY LIVER DISEASE ACTIVITY SCORE (NAS) USING MAGNETIC RESONANCE ELASTOGRAPHY

(71) Applicant: MAYO FOUNDATION FOR MEDICAL EDUCATION AND RESEARCH, Rochester, MN (US)

(72) Inventors: Meng Yin, Rochester, MN (US); Richard L. Ehman, Rochester, MN (US); Alina Allen, Rochester, MN (US); Vijay H. Shah, Rochester, MN (US); Sudhakar K. Venkatesh, Rochester, MN (US); Taofic Mounajjed, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 416 days.

(21) Appl. No.: 15/819,160

(22) Filed: Nov. 21, 2017

(65) Prior Publication Data
US 2018/0140219 A1 May 24, 2018

Related U.S. Application Data

(60) Provisional application No. 62/425,916, filed on Nov. 23, 2016.

(51) Int. Cl.
| | | |
|---|---|---|
| A61B 5/055 | (2006.01) | |
| A61B 5/00 | (2006.01) | |
| G01R 33/563 | (2006.01) | |
| G01R 33/30 | (2006.01) | |
| G06T 11/00 | (2006.01) | |

(Continued)

(52) U.S. Cl.
CPC .............. *A61B 5/055* (2013.01); *A61B 5/004* (2013.01); *A61B 5/0022* (2013.01); *A61B 5/0051* (2013.01); *A61B 5/0816* (2013.01); *A61B 5/318* (2021.01); *A61B 5/4244* (2013.01); *A61B 5/7282* (2013.01); *A61B 5/7285* (2013.01); *G01R 33/30* (2013.01); *G01R 33/56358* (2013.01); *G06T 11/006* (2013.01); *A61B 5/7278* (2013.01); *A61B 5/748* (2013.01); *A61B 2576/02* (2013.01)

(58) Field of Classification Search
CPC ..... A61B 5/055; A61B 5/0022; A61B 5/0816; A61B 5/7285; A61B 5/0402; A61B 5/7282; A61B 5/4244; A61B 5/0051; A61B 5/004; A61B 5/7278; A61B 2576/02; A61B 5/748; G06T 11/006; G01R 33/30; G01R 33/56358
See application file for complete search history.

(56) References Cited

U.S. PATENT DOCUMENTS

| | | |
|---|---|---|
| 5,592,085 A | 1/1997 | Ehman |
| 5,825,186 A | 10/1998 | Ehman et al. |
| 7,034,534 B2 | 4/2006 | Ehman et al. |

(Continued)

*Primary Examiner* — Hien N Nguyen
(74) *Attorney, Agent, or Firm* — Quarles & Brady LLP (57) ABSTRACT

The present disclosure relates to a system and method for non-invasively determining NAFLD activity scores (NAS) in patients using mechanical properties determined through magnetic resonance elastography (MRE) imaging. The non-invasively determined NAS score is then used to diagnose NFALD and NASH patients.

15 Claims, 6 Drawing Sheets

(51) Int. Cl.
    *A61B 5/08*           (2006.01)
    *A61B 5/318*        (2021.01)

(56) References Cited

U.S. PATENT DOCUMENTS

| | | |
|---|---|---|
| 7,307,423 B2 | 12/2007 | Ehman et al. |
| 2009/0299168 A1 | 12/2009 | Ehman et al. |
| 2010/0005892 A1 | 1/2010 | Ehman et al. |
| 2018/0140247 A1* | 5/2018 | Miette .................... A61B 8/485 |

* cited by examiner

SYSTEM AND METHOD FOR GENERATING NONALCOHOLIC FATTY LIVER DISEASE ACTIVITY SCORE (NAS) USING MAGNETIC RESONANCE ELASTOGRAPHY

CROSS-REFERENCE TO RELATED APPLICATIONS

This application is based on, claims priority to, and incorporates herein by reference for all purposes, U.S. Application Ser. No. 62/425,916, filed Nov. 23, 2016, and entitled "SYSTEM AND METHOD FOR GENERATING NONALCOHOLIC FATTY LIVER DISEASE ACTIVITY SCORE (NAS) USING MAGNETIC RESONANCE ELASTOGRAPHY."

STATEMENT REGARDING FEDERALLY SPONSORED RESEARCH

This invention was made with government support under EB001981 and EB017197 awarded by National Institutes of Health. The government has certain rights in the invention.

BACKGROUND

The explosive growth in obesity and type-2 diabetes mellitus worldwide has led to a dramatic increase in the prevalence of nonalcoholic fatty liver disease (NAFLD), which includes a histological spectrum of disease that ranges from simple hepatic steatosis to nonalcoholic steatohepatitis (NASH) with advanced stages of fibrosis. NAFLD is estimated to affect one-third of the general adult population in the United States. Over 25% of these patients are likely to have NASH, which may progress to cirrhosis and conferred a risk of developing HCC. Needle liver biopsy has long been considered the "gold standard" for diagnosing liver injuries. The diagnosis of NASH is defined by the presence and pattern of specific histological abnormalities on liver biopsy. Recently, a semi-quantitative NAFLD activity score (NAS) systems—the unweighted sum of steatosis, lobular inflammation, and hepatocellular ballooning scores—was developed for the diagnosis of NASH based on histological evaluation on liver biopsies. It was developed as a tool to diagnose NASH or measure changes in NAFLD during therapeutic trials. NAS of correlated with a diagnosis of NASH, while NAS<3 were diagnosed as "not NASH". However, this procedure is an expensive diagnostic test ($5 k-$8 k total cost in the USA) and invasive with possible complications (hospitalization in 1-3%, and one death per 10,000 procedures). The accuracy of liver biopsy is also affected by sampling error and subjective scoring system.

Therefore, it would be desirable to have a system and method to perform a NASH diagnosis and perform longitudinal follow-up analysis to meet the increasing concern of NAFLD.

SUMMARY OF THE DISCLOSURE

The present disclosure addresses the aforementioned drawbacks by providing a system and method for non-invasively determining NAFLD activity scores (NAS) in patients using mechanical properties determined through magnetic resonance elastography (MRE) imaging. Specifically, the present disclosure provides a—statistical model that pairs appropriate mechanical properties with associated response NAS features for the determination of the NAS score. The NAS score can then be used to diagnose NAFLD and NASH patients without the need for liver biopsy.

In accordance with one aspect of the disclosure, a method is provided for using an MRI system to non-invasively determine a nonalcoholic fatty liver disease (NAFLD) activity score of a subject for the use in diagnosing hepatic diseases. The method includes controlling a driver to impart an oscillatory motion to the subject to cause a wave motion to propagate through a region of interest including a liver and controlling the MRI system to perform a magnetic resonance elastography (MRE) process to acquiring image data from the subject using a pulse sequence that employs a motion-encoding coordinated with the wave motion propagating through the region of interest. The method also includes reconstructing an elastogram of the region of interest from the image data and calculating the NAFLD activity score of the liver of the subject using the elastogram.

In accordance with another aspect of the disclosure, a magnetic resonance imaging (MRI) system is provided that includes a magnetic system configured to generate a polarizing magnetic field about a region of interest within a liver of a subject and a plurality of gradient coils configured to apply a gradient field to the polarizing magnetic field. The MRI system also includes a radio frequency (RF) system configured to apply an excitation field to the subject and acquire MR image data therefrom and a driver system configured to deliver an oscillatory stress to the subject to, thereby, direct a shear wave toward the region of interest. The MRI system further includes a computer system programmed to control operation of the plurality of gradient coils, RF system, and driver system to acquire medical imaging data, invert medical imaging data to calculate mechanical properties from the region of interest within the liver of the subject, and calculate a nonalcoholic fatty liver disease (NAFLD) activity score using the mechanical properties from the region of interest within the liver of the subject.

In accordance with another aspect of the disclosure, a method is provided for using an MRI system to non-invasively detect hepatic inflammation for the use in diagnosing hepatic diseases. The method includes controlling a driver to deliver generate continuous wave motion to propagate through the region of interest in a subject that includes the liver and controlling the MRI system acquire imaging data by performing a pulse sequence that employs a motion-encoding gradient coordinated with the continuous wave motion propagating through the region of interest including the liver. The method also includes reconstructing wave images from the imaging data, calculating a damping ratio and a loss modulus for the region of interest within the liver using the wave images, and calculating an interstitial fluid volume and an interstitial fluid pressure for the region of interest within the liver using the damping ratio and loss modulus.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

The present disclosure relates to a system and method for performing magnetic resonance elastography ("MRE") to non-invasively determine clinically-accepted information that, historically, has only been able to be derived using interventional procedures and laboratory pathology, such as to derive NAS scores diagnosing NAFLD and NASH patients non-invasively.

Magnetic Resonance Imaging (MRI) offers chemical-shift imaging and spectroscopic methods for the quantification of steatosis, or lipid content, with relatively high accuracy without any invasive procedures or radiation exposure, compared to invasive liver biopsy, qualitative ultrasound and semi quantitative CT approaches. Thus, MRI-assessed fat fraction should be a more accurate imaging biomarker for steatosis extent and can play an important role in NAS prediction. Magnetic Resonance Elastography (MRE) is an MRI-based technology for quantitatively mapping the mechanical properties of tissue. There is increasing evidence leading to an emerging consensus that hepatic MRE is the most reliable non-invasive method for detecting and staging liver fibrosis.

The provided methods differ from traditional NAS score determination in significant ways. First, the traditional method requires a biopsy specimen. As mentioned above, this procedure is expensive and subject to sampling errors. The systems and methods disclosed herein use an MRI system to obtain at least three tissue properties of the tissue sample to non-invasively, objectively, and quantitatively determine a NAS score. As will be discussed below, a statistical model has demonstrated through preclinical and clinical trials to be accurate at determining what pathologists would report as the NAS score.

Figure 1:
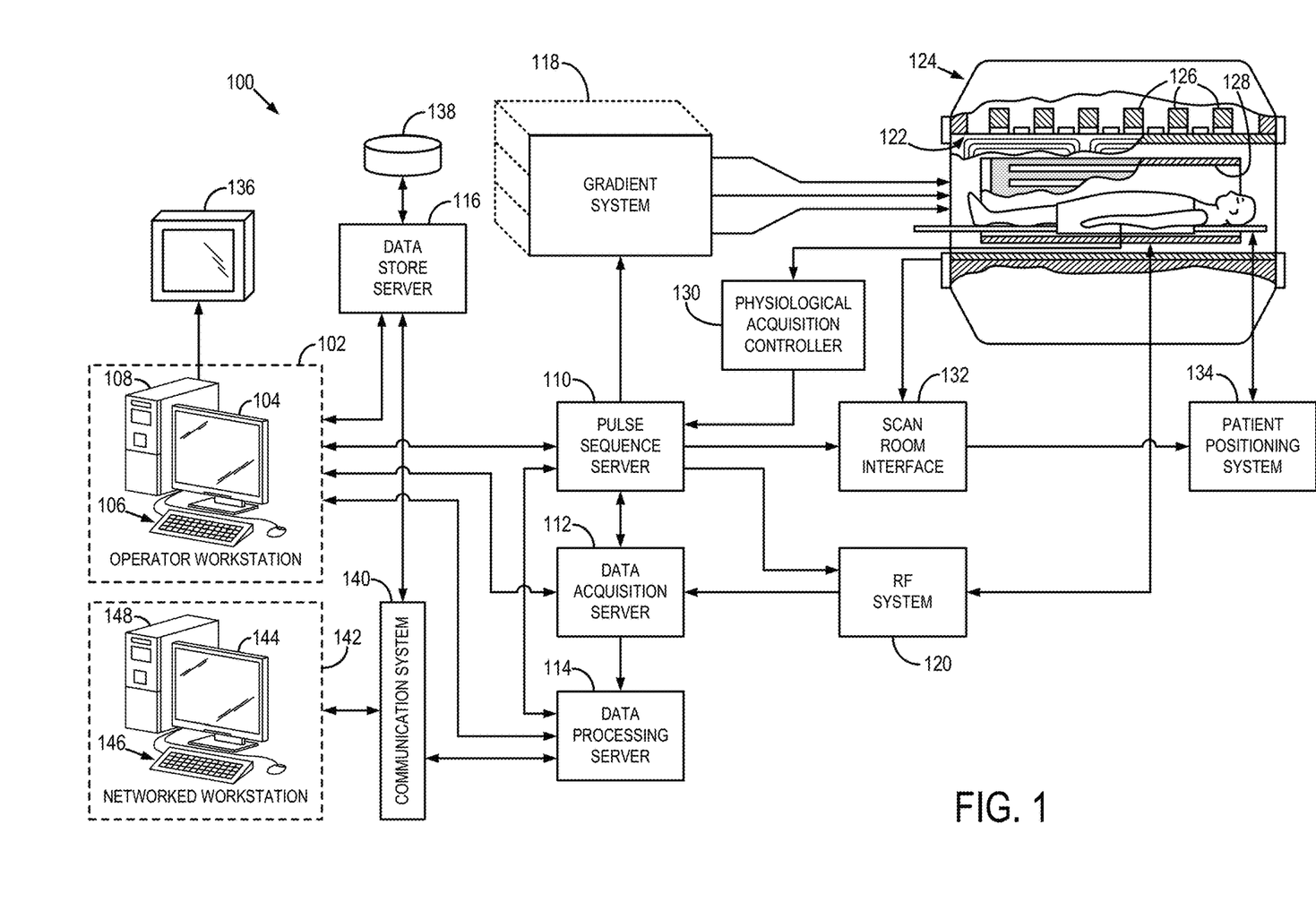
FIG. 1 is a schematic diagram of a magnetic resonance imaging (MRI) system for use with the systems and methods of the present disclosure.

Referring particularly now to FIG. 1, an example of an MRI system 100 that can implement the methods described here is illustrated. The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

In magnetic resonance elastography ("MRE"), an external vibration source generates mechanical waves in a tissue that are used to characterize that tissue. For example, an active or passive acoustic driver is used to generate vibratory motion in the tissue of a subject under examination. The physical properties of tissue are measured using MRE by applying a stress with this vibratory motion and observing the resulting strain. By measuring the resulting strain, elastic properties of the tissue such as Young's modulus, Poisson's ratio, shear modulus, and bulk modulus can be calculated. Moreover, by measuring the strain in multiple directions, the mechanical properties of the tissue can be completely defined.

The attenuation of the strain wave can also be estimated by observing the rate at which the strain decreases as a function of distance from the stress producing source. From this, the damping ratio, loss modulus and viscous properties of the medium may be estimated. The dispersion characteristics of the medium can be estimated by observing the speed and attenuation of the strain waves as a function of their frequency.

Typically, a single slice is imaged with motion-encoding performed in three orthogonal directions in three different acquisitions. Imaging in other planes may also be performed, and multi-slice imaging is also possible. The data acquisition may be performed over several breath holds; however, the acquisition may also be respiratory gated or self-navigated so that the subject can breathe freely during the scan.

Figure 2:
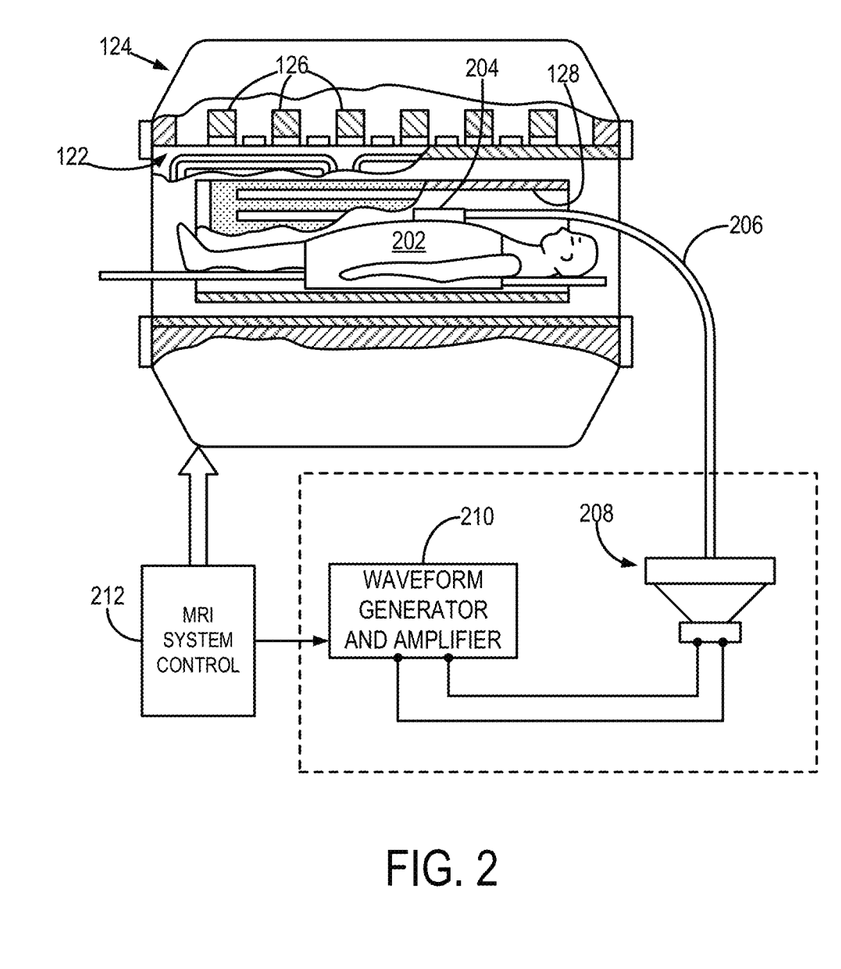
FIG. 2 is a schematic diagram of the MRI system of FIG. 1 configured for operation with a magnetic resonance elastography (MRE) driver system to perform an MRE process.

Referring now to FIG. 2, the MRE driver system of the present invention is a passive driver system that may be placed on a subject 202 and energized to produce an oscillating, or vibratory, stress. The MRE driver system includes a passive driver 204 positioned over a region-of-interest, such as the sternum, in the subject 202 and connected by means of a tube 206 to a remotely located active acoustic driver 208. The active driver 208 is remote from the bore of the magnet assembly 124 in the sense that it is positioned away from the strong magnetic fields produced by the magnet assembly 124 where its operation is not impeded by those fields, and where its operation will not perturb the magnetic fields of the MRI system 100. The active driver 208 is electrically driven by a waveform generator and amplifier 210, which in turn is controlled by the pulse sequence server 110, which forms a part of the MRI system control 212. The MRI system control 212 directs the MRI system 100 to perform an MRE scan by driving the RF coil 128 and the gradient coils 122 in the magnet assembly 124 to perform a series of pulse sequences, while enabling the waveform generator 210 to apply an oscillatory stress to the subject 202 at the proper moment during each pulse sequence, as described in U.S. Pat. No. 5,592,085, which is herein incorporated by reference in its entirety. The active driver 208 and the waveform generator and amplifier 210 may be housed together in a manually portable unit, denoted by dashed line 214. Exemplary active acoustic drivers 208 are disclosed in U.S. Pat. Nos. 7,034,534 and 7,307,423; and in U.S. Patent Application Publications Nos. US2009/0299168 and US2010/0005892.

Using the above-described MRE driver system, the physical properties of tissue, such as the liver, can be measured using MRE by applying a stress to the subject 202 and observing the resulting strain. By measuring the resulting strain, elastic properties of the tissue, such as Young's modulus, Poisson's ratio, shear modulus, and bulk modulus can be calculated. By applying the stress in all three dimensions and measuring the resulting strain, the elastic properties of the tissue can be defined.

By observing the rate at which the strain decreases as a function of distance from the stress producing source, the attenuation of the strain wave can be estimated. From this, the damping ratio, loss modulus and viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

The tube 206 is made of a material which is flexible, yet inelastic. The flexibility enables it to be fed along a winding path between the subject 202 in the magnet 124 and the remote site of the active driver 208. In one configuration, the tube 206 is twenty feet long and has an inner diameter of one inch. The tube 206 may be composed of a clear vinyl material sold under the trademark TYGON and may have a wall thickness of approximately one-eighth inch. TYGON is a registered trademark of Norton Company of Worchester, Mass. Alternatively, the tube 206 may include a polyvinyl chloride ("PVC") tube with a reinforced wall having an inside diameter of approximately three-quarters of an inch. The tube 206 is inelastic such that it does not expand in response to the variations in air pressure caused by the acoustic energy it conveys. As a result, the acoustic energy is efficiently conveyed from the active driver 208 to the passive driver 204.

Figure 3:
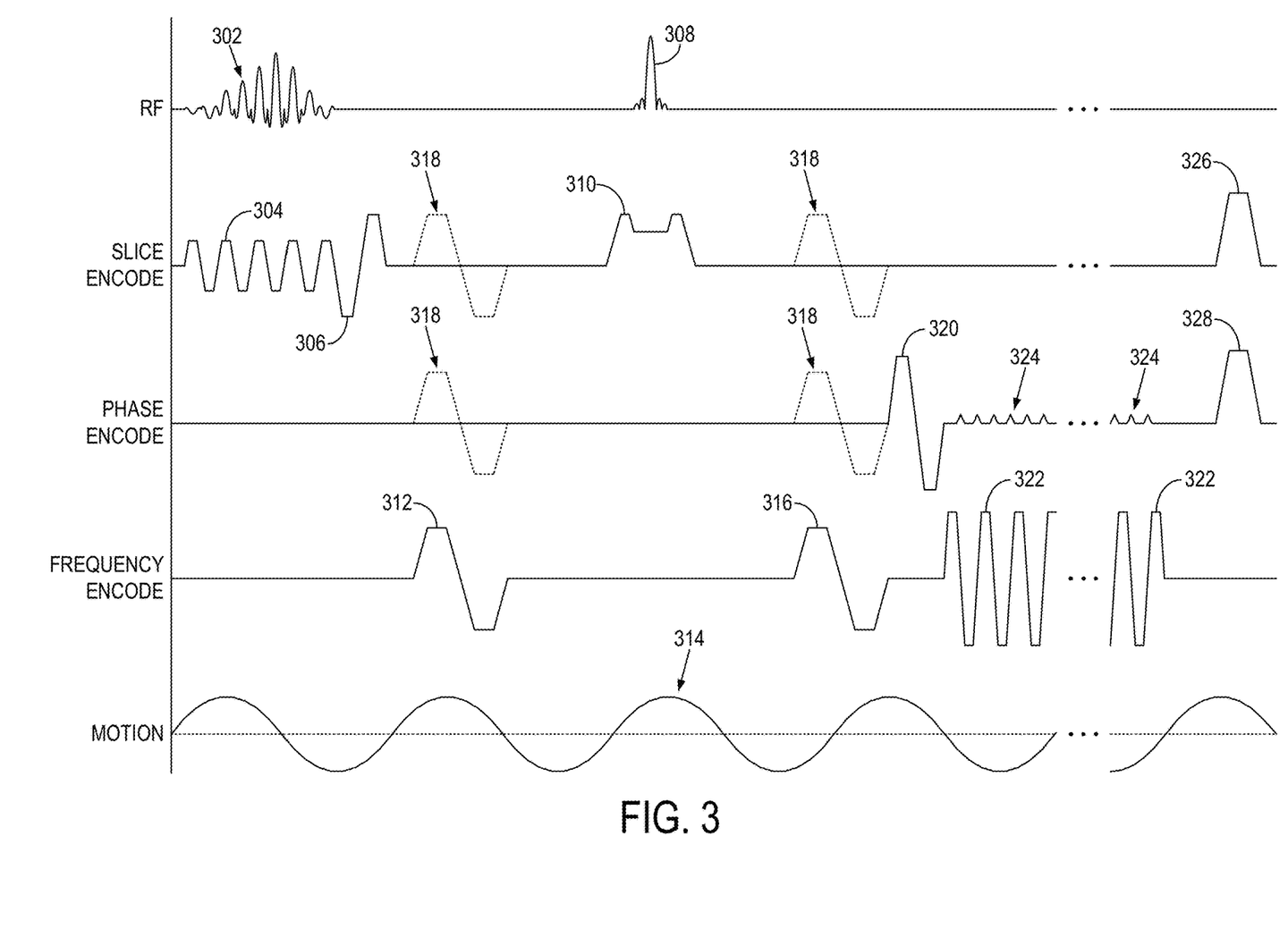
FIG. 3 is a pulse sequence diagram illustrating an MRE pulse for use in determining mechanical properties of the tissue using, for example, the systems of FIGS. 1 and 2.

Referring now to FIG. 3, an exemplary spin-echo echo-planar imaging ("SE-EPI") pulse sequence for acquiring MRE data in accordance with some embodiments of the present invention is illustrated. It should be noted that a SE pulse sequence is provided for exemplary purposes and the present invention may use other pulse sequences, such as gradient echo pulse sequences. The pulse sequence begins with the application of a spatial-spectral radio frequency ("RF") excitation pulse 302 that is played out in the presence of an alternating slice-selective gradient 304. To mitigate signal losses resulting from phase dispersions produced by the slice-selective gradient 304, a rephasing lobe 306 is applied after the slice-selective gradient 304.

A refocusing RF pulse 308 is applied in the presence of another slice-selective gradient 310 to induce the formation of a spin-echo. In order to substantially reduce unwanted phase dispersions, crusher gradients bridge the slice-selective gradient 310. A first motion-encoding gradient 312 is played out along a motion-encoding direction before the refocusing RF pulse 308. The frequency of the motion-encoding gradient 312 is set at or near the center frequency of the motion 314 produced by the MRE driver. By way of example, this multi-frequency of the motion-encoding gradient 312 may be set at 30, 40 and 60 Hz. Following the refocusing RF pulse 308, a second motion-encoding gradient 316 is played out along the motion-encoding direction. For example, as illustrated in FIG. 3, the motion-encoding gradients 312, 316 may be played out along the frequency-encoding direction. In the alternative, as indicted by dashed lines 318, the motion-encoding gradients 312, 316 may be played out along the phase-encoding direction, the slice-encoding direction, or some combination of these three directions so as to encode motion 314 in an oblique direction.

A prephasing gradient 320 is played out along the phase-encoding direction to prepare the transverse magnetization for data acquisition. Then, an alternating readout gradient pulse train 322 is then produced in order to form echo signals from which image data is acquired. For example, gradient-echo signals formed under a spin-echo envelope are acquired during each positive and negative pulse peak of the readout pulse train 322. A phase-encoding gradient "blip" 324 is applied between each readout pulse peak to separately phase encode each acquired gradient-echo signal. Following the conclusion of the readout gradient pulse train 322, a spoiler gradient 326 is played out along the slice-encoding direction and another spoiler gradient 328 is played out along the phase-encoding gradient to prepare the spins for subsequent data acquisitions. The data acquisition is repeated a plurality of times with appropriate changes to the slice selection procedure and applied vibration frequency such that multiple slices of image data are acquired at multiple frequencies. Additionally, separate acquisitions may be performed with the RF center frequency on the water resonance peaks.

Image reconstruction and processing of the reconstructed image may also be performed to provide an indication of tissue stiffness as disclosed in U.S. Pat. No. 5,825,186, which is incorporated herein by reference in its entirety.

Figure 4:
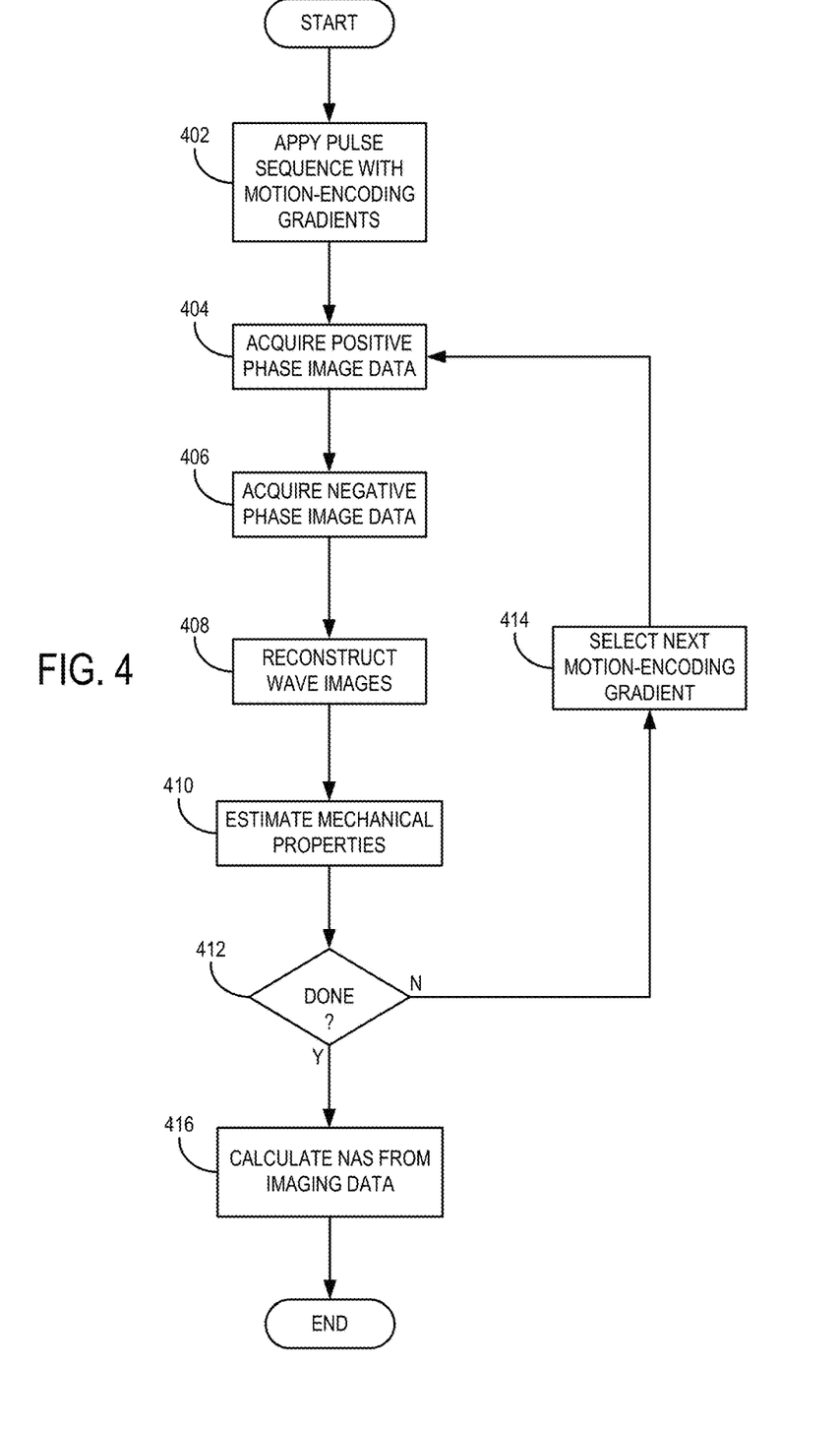
FIG. 4 is a flow chart setting forth some example steps for using an MRE process to non-invasively determine NAS scores.

One aspect of the present disclosure employs the MRI system to measure mechanical properties of the liver to non-invasively determine the NAFLD activity score. Referring now to FIG. 4, a flowchart is illustrated as setting forth the steps of an exemplary method for acquiring image data, reconstructing image data, estimating mechanical properties of a tissue, and determining the NAFLD activity score (NAS).

Data are acquired from a subject with a magnetic resonance imaging ("MRI") system using a pulse sequence that uses motion-encoding gradients to encode vibratory motion that has been imparted to a tissue-of-interest in the subject, as indicated at step 402. The vibratory motion can be imparted using an active acoustic driver or a passive acoustic driver, as discussed above. In some instances, an acoustic driver is not used and instead the vibratory motion can be transient motion, such as motion that is imparted to the tissue-of-interest by way of the subject's beating heart or respiratory movement. In another instance, the driver system is a pneumatic-based pressure-activated driver and is arranged on the subject such that it is proximal to the liver.

As an example data acquisition, positive phase data are acquired using an acquisition such as the one in FIG. 3, as indicated in step 404. In this acquisition, the polarity of the motion-encoding gradients is selected to be in-phase with the imparted motion. Following the acquisition of the positive phase image data, the negative phase data are acquired, as indicated in step 406. In this acquisition, the polarity of the motion-encoding gradients is inverted, such that the motion-encoding gradient is out-of-phase with the imparted motion. After all the desired image data has been acquired, wave images are reconstructed from the positive and negative phase image data sets, as indicated at step 408. The wave images are then used to calculate the mechanical properties of the tissue, as indicated at step 410, and in accordance with traditional MRE techniques.

A decision is then made at step 412 of whether to apply another motion encoding gradient at step 414 to calculate more mechanical properties of the tissue. In one non-limiting example, at least two mechanical properties may be calculated to correspond to the two dependent NAS variables (i.e., inflammation and ballooning). In some non-limiting examples, the mechanical properties can comprise liver stiffness, damping ratio, storage modulus, loss modulus, frequency dispersion, volumetric strain and nonlinearity constants. In another aspect, particular mechanical properties were found to favorably correlate to the NAS dependent variables. These NAS parameters include steatosis, liver inflammation, and hepatocellular ballooning. Steatosis is mainly associated with fat fraction. It is not a significant confounding factor to many mechanical properties of the liver, such as liver stiffness, storage modulus, loss modulus and damping ratio.

As mentioned above, MR offers chemical-shift imaging and spectroscopic methods for accurate quantification of steatosis, or lipid content. In other words, MRI-assessed fat fraction is an accurate tissue property that can be used to estimate steatosis extent. Furthermore, it is an important parameter in NAS determination. In another aspect, the damping ratio is highly correlated with early inflammation before the onset of significant liver injuries. In other words, the damping ratio can be used as an accurate mechanical property for liver inflammation. In another aspect, hepatocellular ballooning can be highly correlated with subsequent cellular death and extracellular matrix remodeling, or fibrosis. Mechanically speaking, it is the "broken" point in NAFLD disease progress. Therefore, liver stiffness or nonlinear elasticity is an effective mechanical property to correlate to hepatocellular ballooning.

In another aspect, nonlinearities can be the 3rd and 4th-order constants that are calculated with MRE imaging. They can differentiate what level of deformation or stress the perturbations are applied, and are applicable to that pathophysiologic state. In the liver with NASH, hepatocellular ballooning causes overstress in the cells, which is related to the cellular malfunction, structure remodeling and even death. Similar to liver stiffness, 3rd and 4th-order constants correlate to hepatocellular ballooning.

Thus, at step 416 the NAS score is determined from the acquired image data or, more particularly, the derived mechanical properties reflected in the image data. In accordance with one non-limiting example, a formula for calculating a NAS score from an elastogram or other imaging data having sufficient information about mechanical properties of a region of interest may be similar to the method illustrated below.

First of all, data reduction and feature extraction is performed to generate a smaller set of predictors that seek to capture majority information in the original variables. Principal component analysis is used as the linear combination of the predictors for NAS score. Mathematically, the jth PC is written as: $PC_j=(a_{j1} \times \text{Predictor 1})+(a_{j2} \times \text{Predictor 2})+ \ldots +(a_{jP} \times \text{Predictor P})$. P is the number of predictors. The coefficients $a_{j1}, a_{j2}, \ldots, a_{jP}$ are called component weights for NAS prediction model. Cross-validation is used to determine the optimal number of predictors to retain that minimize root mean squared error. Given that mean squared error is a combination of variance and bias, it is very possible to produce models with smaller mean squared errors by allowing the parameter estimates to be biased. A lasso model or a generalized lasso model (elastic net) can be used to combine one or two penalties to ridge regression by making a trade-off between the model variance and bias. The sum of the squared regression parameters is written as:

$$SSE_L = \Sigma_{i=1}^n (y_i - \hat{y}_i)^2 + \lambda \Sigma_{j=1}^P |\beta_j|; \text{ or} \quad (3).$$

$$SSE_{Enet} = \Sigma_{i=1}^n (y_i - \hat{y}_i)^2 + \lambda_1 \Sigma_{j=1}^P \beta_j^2 + \lambda_2 \Sigma_{j=1}^P |\beta_j| \quad (4).$$

where SSE is the sum of squared error; $y_i$ is the ith observed value of the outcome, $\hat{y}_i$ is the predicted outcome of the ith data point, i=1, 2, ... n. n is the number of data points; P is the number of predictors; $\lambda$ is the lasso penalty; $\beta$ is an unknown or theoretical model coefficient. These models can effectively deal with groups of high correlated predictors of tissue mechanical properties.

Thus, a construct is provided that incorporates, for example, two tissue parameters, such as stiffness and damping ratio, obtained from MRE data and an MRI-based measurement of fat content, to generate a NAS score derived without interventional procedures. Again, the NAS score is based on a numeric values that are subjectively assigned by the pathologist for fat, inflammation, fibrosis, and cellular ballooning. And those subjective numbers are added up to generate the "NAS score", which is regarded as the gold standard for diagnosing NASH. Here, the need to interventionally acquire tissue samples for laboratory pathology and then rely on the subjectivity of pathologist scoring is removed in favor of a non-interventional, process.

As a further example, the selected mechanical properties may be used in a statistical model to determine the NAS score. In some aspects, the mechanical properties can be a multi-dimensional vector of NASH features or NAS predictors, and fat fraction and each mechanical property can be the response variable to steatosis, inflammation, hepatocellular ballooning and fibrosis extents of the liver.

Figure 5A:
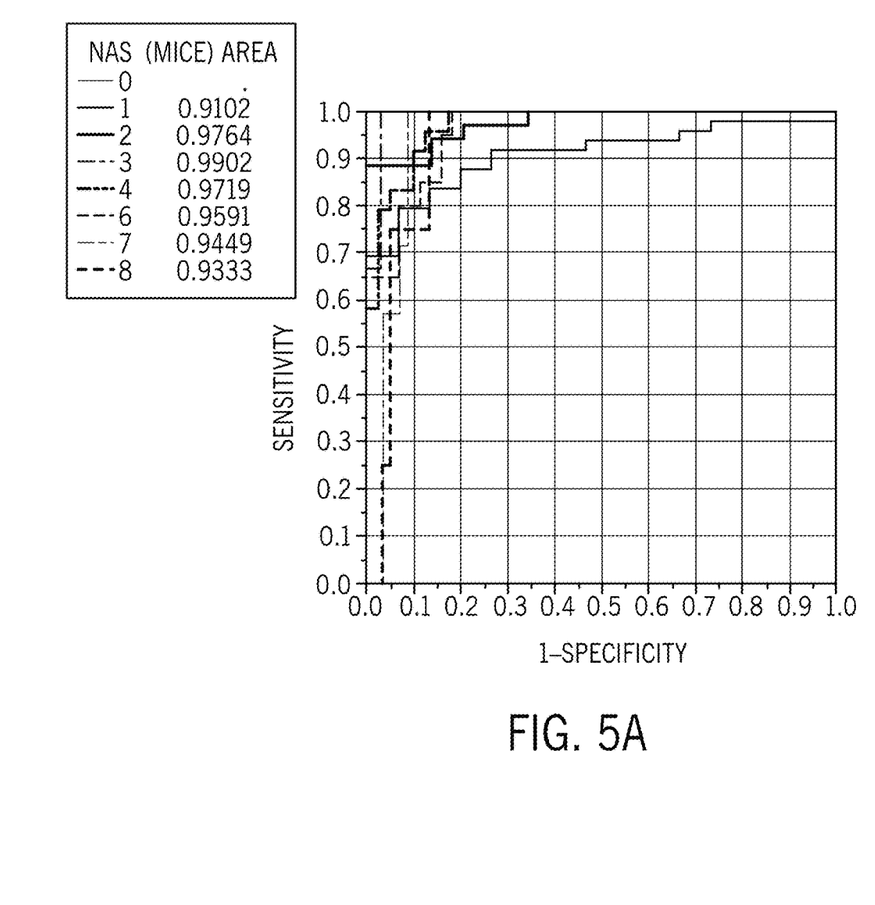
FIG. 5A is a graphs showing results from an ROC analysis of NAS score determination using three tissue property parameters in a preclinical trial of 64 mice.
Figure 5B:
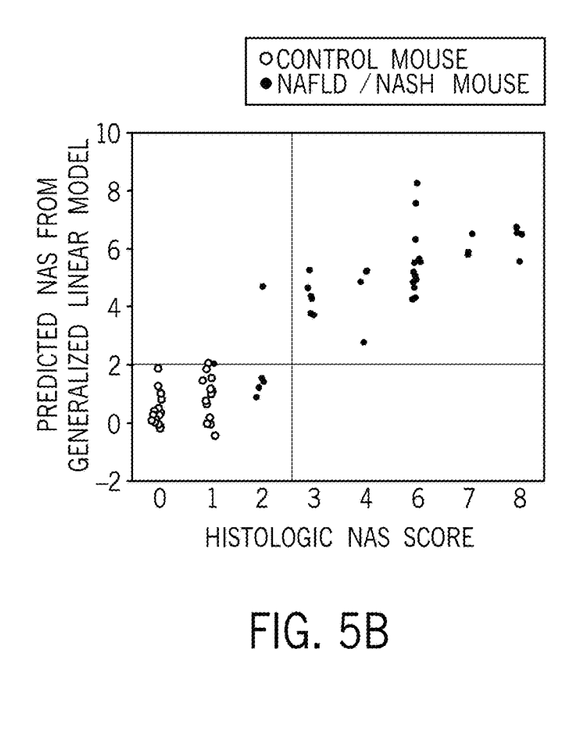
FIG. 5B is a scatter plot of NASH classification using the statistical model in a preclinical trial of 64 mice.
Figure 5C:
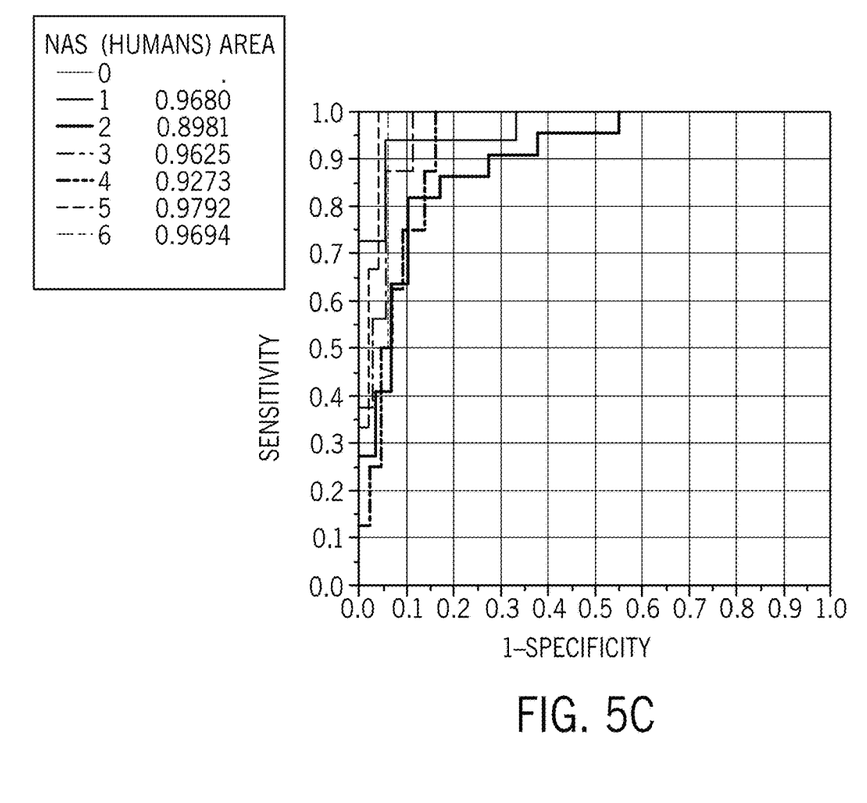
FIG. 5C is a graph showing results from an ROC analysis of NAS score determination using three mechanical property parameters in a clinical trial of 38 patients and 13 volunteers.
Figure 5D:
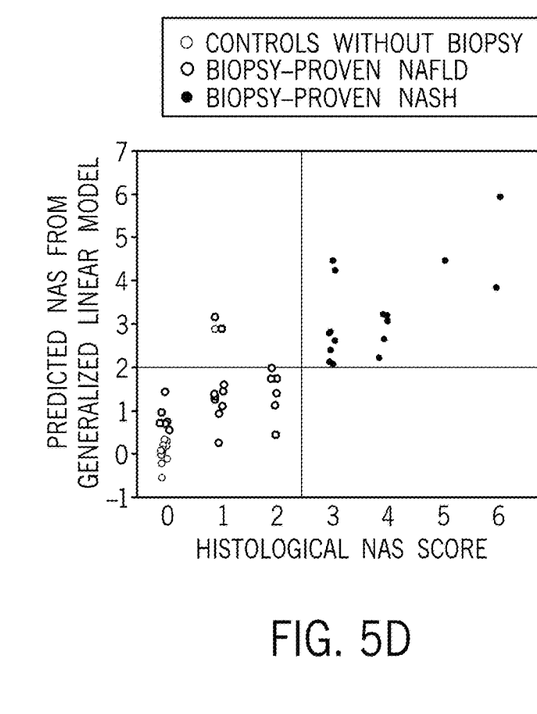
FIG. 5D is a scatter plot of NASH classification using the statistical model in a clinical trial of 38 patients and 13 volunteers.

For example, FIGS. 5A-5D provide data demonstrating the accuracy and clinical utility for deriving NAS scores non-invasively using image data acquired using MRE. Specifically, FIGS. 5A-D provide graphs from two examples of using the statistical model to determine NAS scores for noninvasively diagnosing NAFLD and NASH in preclinical mice trials and clinical trials. FIGS. 5A and 5B show the statistical model on a preclinical data set of 64 mice. FIGS. 5C and 5D show the statistical model on a clinical data set of 38 patients and 13 volunteers.

Regression results show exceptional correlation with pathology analysis for interventionally-derived/biopsy samples and, thus, demonstrate clinical utility. Each mechanical property in the statistical model was paired with one of the three NAS features. As discussed above, fat fraction, damping ratio, and liver stiffness were the assumed associated response to steatosis, inflammation, and hepatocellular ballooning, respectively. All the tested three mechanical properties—liver stiffness, damping ratio, fat fraction—show significant effects on the outcomes (p<0.05). Only few false positive misclassifications were observed, as shown in the colored block areas in charts FIG. 5B and FIG. 5D. There were only two failures in 64 mice, and three failures in 51 humans. These failures can be explained. First, histologically-assessed NAS score could be subjective and has potential sampling errors. Second, the method adopted in our preclinical study can cause local ischemia and acute inflammation in the liver tissue. Third, normal volunteers—as shown in green dots in FIG. 5D—could have undiagnosed liver disease.

In another aspect, the statistical model was able to non-invasively detect early hepatic inflammation. For example, in one mouse model of autosomal polycystic kidney disease (ARPKD) studies, animals having inborn disease did not show histologically detectable hepatic inflammation before the age of 3 months old. Conventional liver stiffness measurement cannot distinguish hepatic inflammation from hepatic fibrosis. In our proposed statistical model, both damping ratio and loss modulus increased at the age as early as 1 month old. These mechanical properties were then used to detect liver inflammation much earlier than histologically detectable cellular invasion, because they reflect early changes in interstitial fluid volume and pressure prior to histologically detectable cellular invasion during hepatic inflammation.

Thus, a system and method is provided for non-invasively determining NAFLD activity scores (NAS) in patients using mechanical properties determined through magnetic resonance elastography (MRE) imaging. Specifically, the present disclosure provides a—statistical model that pairs appropriate mechanical properties with associated response NAS features for the determination of the NAS score. The NAS score can then be used to diagnose NAFLD and NASH patients without the need for liver biopsy.

The present disclosure has described one or more preferred embodiments, and it should be appreciated that many equivalents, alternatives, variations, and modifications, aside from those expressly stated, are possible and within the scope of the invention.

The invention claimed is:

1. A method for using an MRI system to non-invasively determine a nonalcoholic fatty liver disease (NAFLD) activity score of a subject for use in diagnosing hepatic diseases, the steps of the method comprising:
   a) controlling a driver to impart an oscillatory motion to the subject to cause a wave motion to propagate through a region of interest including a liver;
   b) controlling the MRI system to perform a magnetic resonance elastography (MRE) process to acquire image data from the subject using a pulse sequence that employs motion-encoding coordinated with the wave motion propagating through the region of interest;
   c) reconstructing an elastogram of the region of interest from the image data; and
   d) calculating the NAFLD activity score of the liver of the subject using the elastogram by:
      calculating a plurality of mechanical properties from the elastogram;
      performing data reduction and feature extraction on the plurality of mechanical properties in order to generate predictors with component weights for each of the generated predictors; and
      calculating the NAFLD activity score as a combination of the generated predictors using a principal component analysis with a linear combination of the generated predictors,
      wherein the plurality of mechanical properties includes at least three mechanical properties comprising tissue stiffness, damping ratio, fat fraction, volumetric strain, frequency dispersions, $3^{rd}$ order nonlinearity constants, and $4^{th}$ order nonlinearity constants.

2. The method of claim 1, wherein step (d) includes using a statistical model to calculate the NAFLD activity score using the at least three mechanical properties of the liver.

3. The method of claim 2, wherein step (d) includes calculating the NAFLD activity score using at least three of the mechanical properties derived from the elastogram as associated response variables from the region of interest.

4. The method of claim 3, wherein the liver stiffness is a response variable for cellular ballooning.

5. The method of claim 3, wherein MRE nonlinearity constants are a response variable for cellular ballooning.

6. The method of claim 3, wherein the damping ratio is a response variable for inflammation.

7. The method of claim 3, wherein the fat fraction is a response variable for steatosis.

8. The method of claim 1, further comprising generating a report indicating at least one of simple hepatic steatosis and nonalcoholic steatohepatitis (NASH) using the NAFLD activity score.

9. The method of claim 1, further comprising generating a report showing the NAFLD activity score as a longitudinal measure of changes in NAFLD.

10. A magnetic resonance imaging (MRI) system comprising:
    a magnetic system configured to generate a polarizing magnetic field about a region of interest within a liver of a subject;
    a plurality of gradient coils configured to apply a gradient field to the polarizing magnetic field;
    a radio frequency (RF) system configured to apply an excitation field to the subject and acquire MR image data therefrom;
    a driver system configured to deliver an oscillatory stress to the subject to, thereby, direct a shear wave toward the region of interest;
    a computer system programmed to:
       control operation of the plurality of gradient coils, RF system, and driver system to acquire medical imaging data;
       invert medical imaging data to calculate at least three mechanical properties from the region of interest within the liver of the subject that include tissue stiffness, damping ratio, fat fraction, volumetric strain, frequency dispersions, 3rd order nonlinearity constants, and 4th order nonlinearity constants; and
       calculate a nonalcoholic fatty liver disease (NAFLD) activity score using the at least three mechanical properties from the region of interest within the liver of the subject by performing data reduction and feature extraction on the mechanical properties with component weights for each of the generated predictors in order to generate predictors, and calculating the NAFLD activity score as a combination of the generated predictors using a principal component analysis with a linear combination of the generated predictors.

11. The system of claim 10, wherein the computer system is further programmed to use a statistical model to calculate the NAFLD activity score using the at least three mechanical properties of the liver.

12. The system of claim 11, wherein the at least three tissue properties include the liver stiffness as a response variable for cellular ballooning, MRE nonlinearity constants as a response variable for cellular ballooning, the damping ratio as a response variable for inflammation, or the fat fraction as a response variable for steatosis.

13. The system of claim 10, wherein the computer system is further programmed to generate a report indicating at least one of simple hepatic steatosis and nonalcoholic steatohepatitis (NASH) using the NAFLD activity score.

14. The system of claim 10, wherein the computer system is further programmed to generate a report showing the NAFLD activity score as a longitudinal measure of changes in NAFLD.

15. The system of claim 10 wherein the computer system is further programmed to calculate the damping ratio and a loss modulus for the region of interest within the liver using the medical imaging data after inversion.

\* \* \* \* \*